(12) United States Patent
Brine, III et al.

(10) Patent No.: US 7,823,217 B2
(45) Date of Patent: Nov. 2, 2010

(54) FACE AND EYE GUARD DEVICE

(75) Inventors: William H. Brine, III, Hopkinton, MA (US); Jonathan Baker, Thornton, NH (US); Eric Darnell, South Strafford, VT (US); Steve Moore, Liverpool, NY (US); Joel Robinson, Oswego, NY (US); Barclay Moore, Homewood, CA (US)

(73) Assignee: Sport Helmets, Inc.

( * ) Notice: Subject to any disclaimer, the term of this patent is extended or adjusted under 35 U.S.C. 154(b) by 311 days.

(21) Appl. No.: 12/007,507

(22) Filed: Jan. 11, 2008

(65) Prior Publication Data
US 2009/0178185 A1 Jul. 16, 2009

(51) Int. Cl.
*A41D 13/00* (2006.01)
(52) U.S. Cl. .................................... 2/9; 2/425
(58) Field of Classification Search ............... 2/9, 2/10, 12, 13, 15, 410, 424, 431, 433, 439, 2/440, 442, 445; 128/858
See application file for complete search history.

(56) References Cited

U.S. PATENT DOCUMENTS

| | | | | |
|---|---|---|---|---|
| 5,911,308 | A * | 6/1999 | Chafitz et al. | 2/9 |
| 6,598,234 | B1 * | 7/2003 | Brown et al. | 2/9 |
| 2007/0226882 | A1 * | 10/2007 | Ryan | 2/426 |
| 2008/0016600 | A1 * | 1/2008 | Hahn et al. | 2/15 |
| 2008/0066208 | A1 * | 3/2008 | Tagliente | 2/9 |

* cited by examiner

*Primary Examiner*—Katherine Moran
(74) *Attorney, Agent, or Firm*—H. Jay Spiegel

(57) ABSTRACT

The eye guard, while complying with ASTM F803-03, has been ergonometrically designed to comfortably fit on the user's face, and to provide openings for the eyes allowing clear vision while at the same time protecting the eyes from impacts from a lacrosse ball. The eye openings are completely open and have dimensions intended to preclude a lacrosse ball from passing therethrough. The upper edges of the eye openings are displaced rearwardly with respect to the lower edges a sufficient distance to preclude a lacrosse ball from striking the two edges simultaneously in a direction that could possibly cause an eye impact. That displacement is specifically devised to cause a lacrosse ball striking one or the other of the edges to be deflected away from the eyes of the player. The upper edge of the eye openings also defines the lower edge of a visor surface. That visor surface transitions from the openings to the rearward edge of the eye guard where it engages the face of the user above the eyes. Below the eye openings, additional openings are provided that are shaped to be aesthetically pleasing and also create a nose engaging portion designed to surround upper portions of the nose. Temples are preferably molded of a flexible material and may include a unique attachment device for an elastic band used to hold the eye guard on the head of the user.

20 Claims, 6 Drawing Sheets

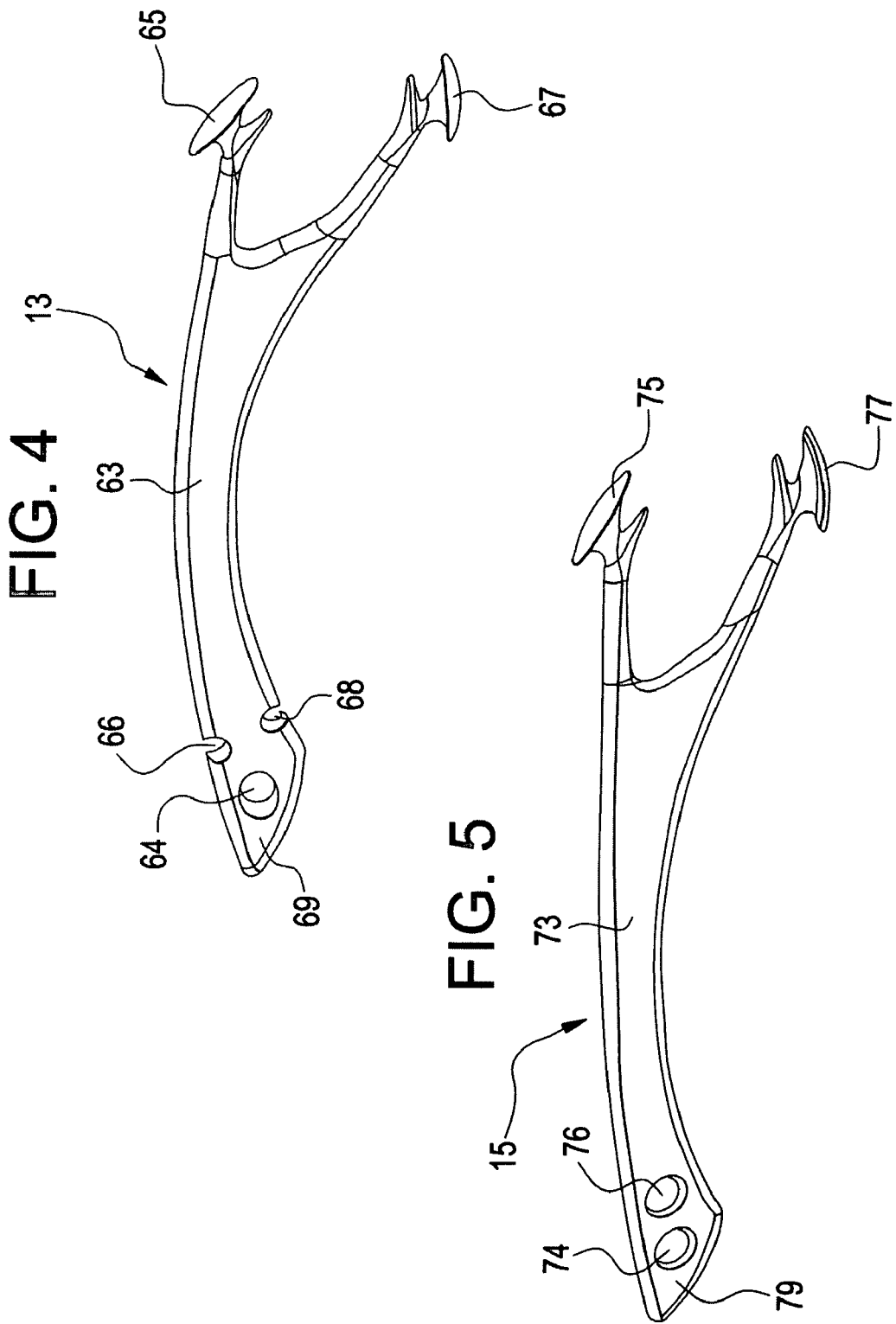

FACE AND EYE GUARD DEVICE

BACKGROUND OF THE INVENTION

The present invention relates to a face and eye guard device. The principles of the present invention are mainly pertinent to the game of lacrosse and particularly women's lacrosse where protective headgear is not required to be worn, but eye protection is necessary.

In the game of women's lacrosse, as reported at www.uslacrosse.org, protective eye wear became required on or after Jan. 1, 2005. As reported at that website, the purpose of that rule is to acknowledge "that while women's lacrosse is a comparatively safe sport, the use of protective eye wear will prevent the rare but catastrophic eye injury at every level of play."

Protective eye wear qualified for use in the game of women's lacrosse is required to meet the most current standard ASTM F803-03 which states that protective eye wear should withstand forces generated by a ball traveling 45 miles per hour for youth play, and 60 miles per hour for adult play defined as high school and older. Such eye wear must not only meet the current ASTM specification standard, but U.S. lacrosse is also required to receive independent confirmation from a third party testing facility recommended by the Protective Eyewear Certification Council (PECC), and the eye wear must also meet the standards of the American Association of Laboratory Accreditation (A2LA).

The present invention has been designed to comply with ASTM Standard F803-03.

Prior art protective eye wear includes devices consisting of steel wire face masks and plastic spectacles. Problems and deficiencies in prior art devices are numerous. These include the weight of protective eye wear and the high cost of manufacture, particularly in association with welded steel wire face masks. In the case of Plano plastic eye wear, a severe problem involves fogging of the plastic lens. As such, wire guards are those most favored in the marketplace today because they don't fog or scratch. Of course, wire guards diminish vision. Plano plastic eye guards are preferred by some due to their light weight and relatively low cost, but their lenses cloud up and scratch.

If it were possible to combine the best features of plastic eye guards, namely, light weight and low cost with the best features of wire eye guards, namely, lack of fogging and scratching, a distinct improvement in eye protection for the game of women's lacrosse would be achieved. It is with these thoughts in mind that the present invention was developed.

SUMMARY OF THE INVENTION

The present invention relates to a face and eye guard device. The present invention includes the following interrelated objects, aspects and features:

(1) In a first aspect, while the inventive face and eye guard device is specifically disclosed as intended for use by women playing the game of women's lacrosse, the present invention is also applicable in other sports such as field hockey, basketball, softball, tennis, racketball, badminton, and others. The specific dimensions of the eye openings of the present invention and relationship between edges of those openings are specifically devised, in preferred embodiments disclosed herein, based upon the dimensions of the ball used in women's lacrosse. In applying the teachings of the present invention to other sports in which a variety of projectiles are used, those dimensions may suitably be altered in accordance with the teachings of the present invention to adapt protective eye wear to those sports.

(2) In a further aspect, as required by U.S. lacrosse and reported at www.uslacrosse.org, since Jan. 1, 2005, players of the game of women's lacrosse have been required to wear protective eye wear satisfying the standard ASTM F803-03. As explained earlier, this standard requires that such protective eye wear must withstand forces generated by a lacrosse ball traveling 45 miles per hour for youth play and 60 miles per hour for adult play defined as high school and older. The present invention complies with this ASTM standard.

(3) The present invention has been ergonometrically designed to comfortably fit on the user's face, and to provide openings for the eyes allowing clear vision while at the same time protecting the eyes from impacts from a lacrosse ball. In order to avoid the issue of fogging, no lenses of any kind are employed. Rather, the eye openings are completely open and have dimensions intended to preclude a lacrosse ball from passing therethrough.

(4) When a lacrosse ball impacts on a hard object at 60 miles per hour, the ball significantly deforms including changing from a spherical shape to a slightly oblong shape. Thus, it is important for the eye guard to not only include dimensions precluding a ball from "squirting" through the eye openings, but also to facilitate deflection of the ball. In this regard, one important feature of the present invention is that the edges of the eye openings are displaced rearwardly with respect to the lower edges a sufficient distance to preclude a lacrosse ball from striking the two edges simultaneously in a direction that could possibly cause an eye impact. Rather, that displacement is specifically devised to cause a lacrosse ball striking one or the other of the edges to be deflected away from the eyes of the player.

(5) The upper edge of the eye openings also defines the lower edge of a top visor surface of the eye guards. That top visor surface transitions from the openings to the rearward edge of the eye guard where it engages the face of the user above the eyes. That portion of the eye guard also serves as a sun visor. Given the spacing between the eyes of the user and the eye openings of the inventive eye guard, the size of the visor portion is significant and effective.

(6) The distance between the eye openings and the eyes creates a significant distance between the forehead where the rear edge of the visor surface engages the forehead and the forward edges of the visor surface. This creates a significant spacing between any point of ball contact and the forehead. This structure also helps deflect a ball that might strike the upper edge over the head of the user rather than deflecting the ball into the head of the user above the forehead.

(7) Below the eye openings, additional openings are provided that are shaped to be aesthetically pleasing and also create a nose engaging portion designed to surround upper portions of the nose. To the rear of the eye guard, padding may be provided on the upper surface downwardly depending from the rear edge of the visor portion and on a lower surface extending upwardly from a lower edge to either side of the nose engaging portion. Such padding may be made of any desired material including a foam that may also have a thin outer skin enclosing a foam center to aid in comfort for the wearer.

(8) The temples of the eye guard are preferably molded of a flexible rubbery material such as, for example, Dupont HYTRAL™. Each temple includes an underlying curvature to best adapt to top surfaces of the ears and forward attachment members consisting of two elongated "fish hook"

shapes designed to fit within corresponding recesses at the side edges of the portion of the eye guard having the eye openings therethrough.

(9) In a further aspect, the temples for the inventive device may include a unique attachment device for an elastic band used to hold the eye guard on the head of the user. In this regard, one temple may include two distal openings with a second temple including a single distal opening and two grooves. In this way, as shown in the drawings, an elastic band may be suitably installed and easily adjusted to accommodate to heads of differing sizes.

(10) In the preferred embodiment of the present invention, materials such as an impact modified polycarbonate and a polycarbonate/PBT alloy may be employed.

As such, it is a first object of the present invention to provide a face and eye guard device.

It is a further object of the present invention to provide such a device made in a lightweight fashion, but providing protection complying with ASTM standard F803-03.

It is a still further object of the present invention to provide such a device in which eye openings are not closed with plastic lenses, but provide protection for the eyes of the user.

It is a still further object of the present invention to provide such a device including eye openings with upper and lower edges designed to deflect a lacrosse ball and preclude it from squeezing therethrough and striking the eyes of the user.

It is a yet further object of the present invention to make such a device that is strong but lightweight, while also being aesthetically pleasing.

These and other objects, aspects and features of the present invention will be better understood from the following detailed description of the preferred embodiment when read in conjunction with the appended drawing figures.

BRIEF DESCRIPTION OF THE DRAWINGS

FIG. 4 shows the left temple of the present invention.

FIG. 5 shows the right temple of the present invention.

SPECIFIC DESCRIPTION OF THE PREFERRED EMBODIMENT

Figure 1:
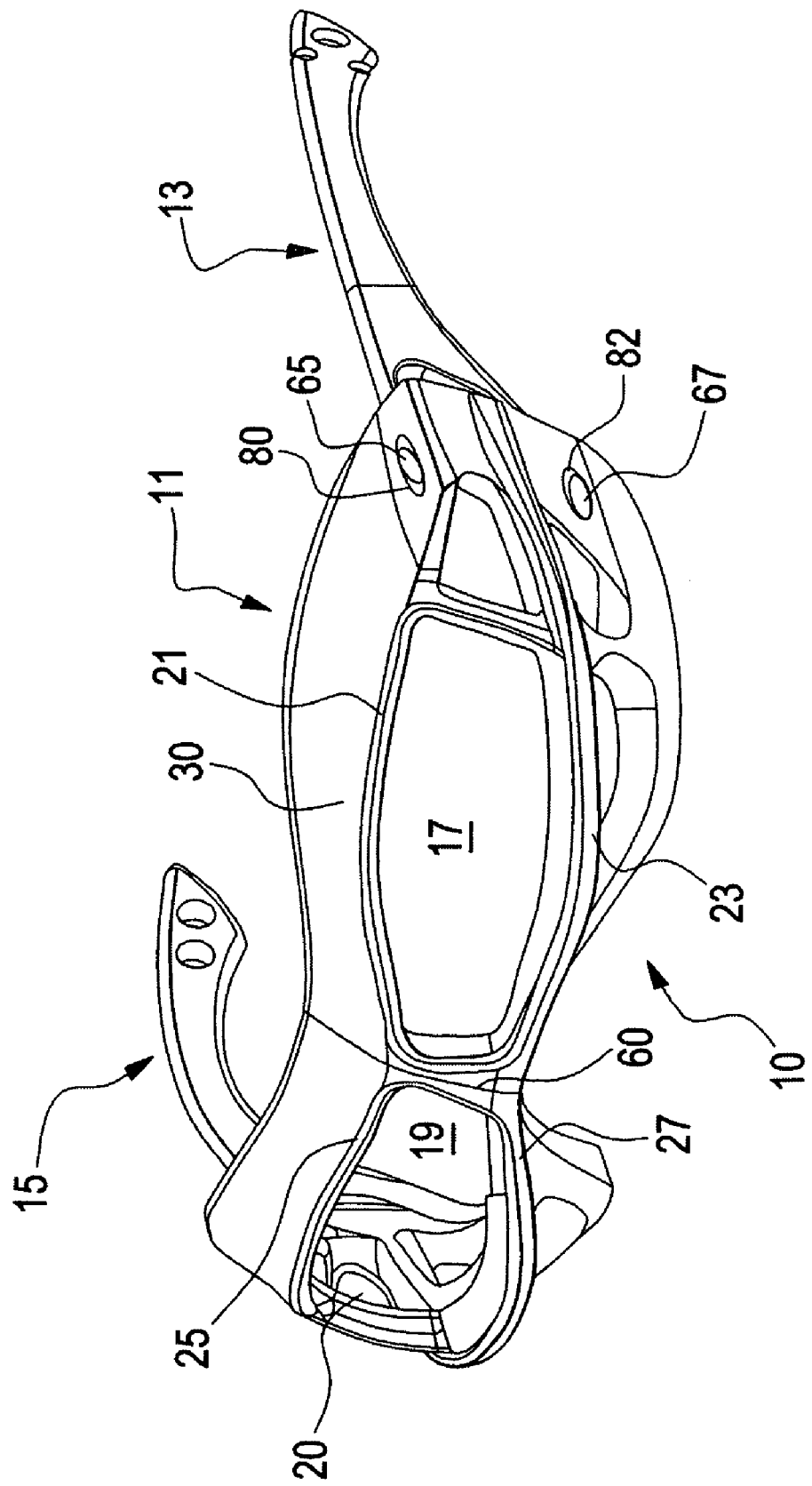
FIG. 1 shows a front left side perspective view of the present invention.
Figure 2:
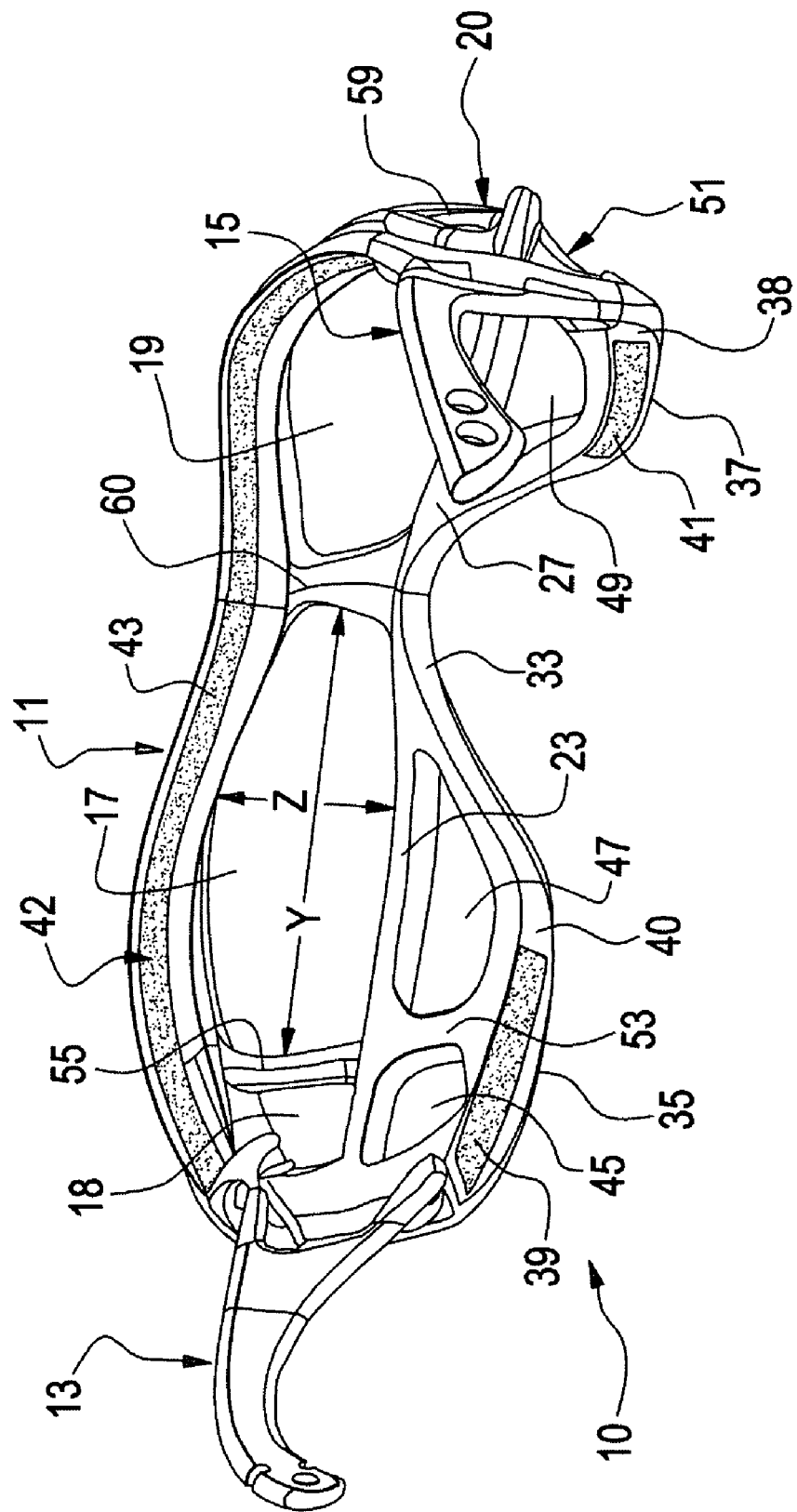
FIG. 2 shows a rear right perspective view of the present invention.

With reference first to FIGS. 1 and 2, the inventive face and eye guard device is generally designated by the reference numeral 10 and includes a guard device 11 as well as a left temple 13 and a right temple 15.

The guard device 11 includes an opening 17 for the left eye of the wearer and an opening 19 for the right eye of the wearer.

Figure 3:
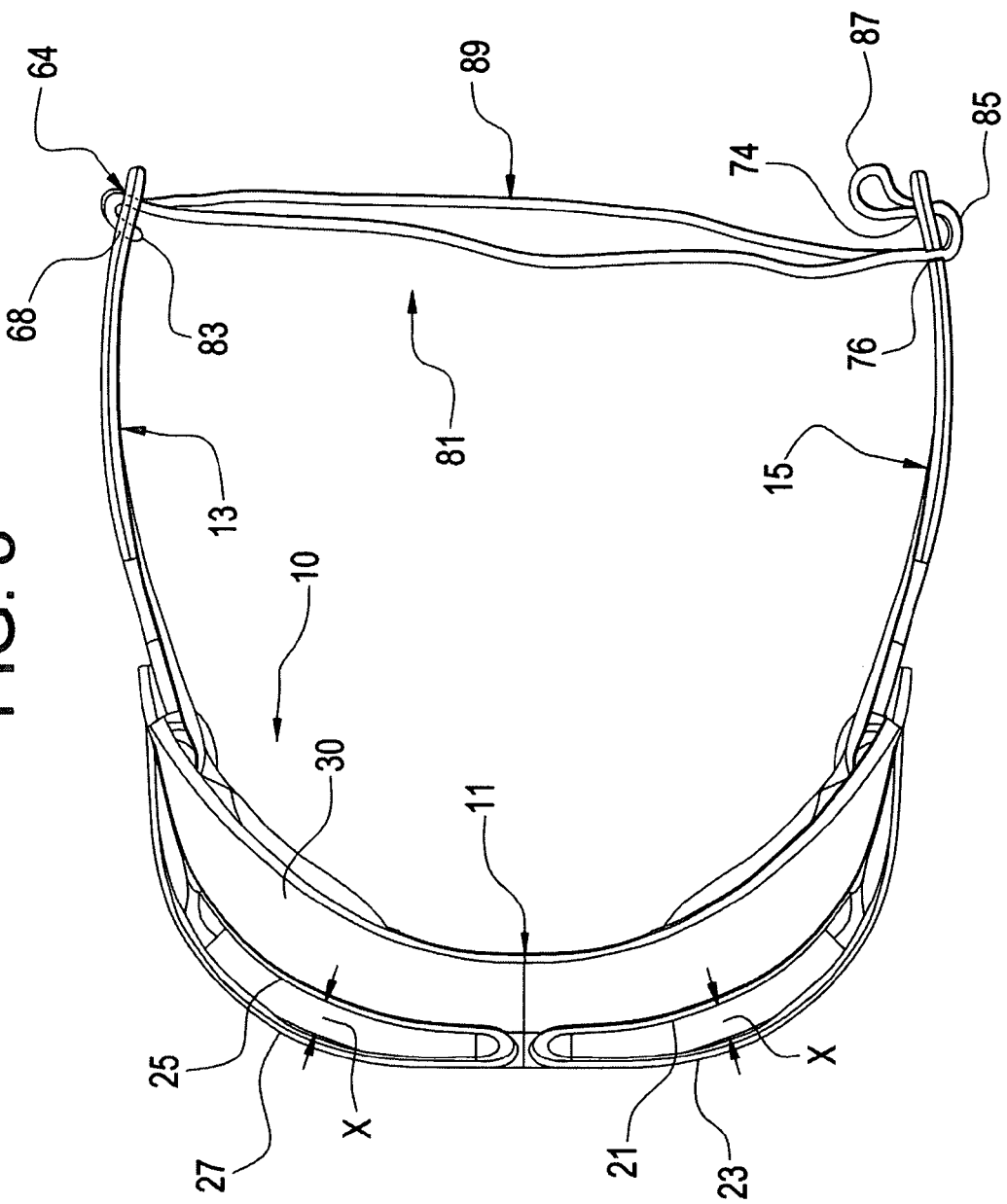
FIG. 3 shows a top view of the present invention.

With reference to FIG. 1, the left eye opening 17 includes an upper edge or bar 21 and a lower edge or bar 23, both of which are generally horizontal. Similarly, the right eye opening 19 includes an upper edge or bar 25 and a lower edge or bar 27, both of which are horizontal. With reference to FIG. 3, it is seen that the lower edges 23 and 27 are displaced forwardly of the upper edges 21 and 25, respectively, by a distance X. The distance X has been experimentally determined so that any impact on the device 10 in the direction of an eyeball will likely only engage one or the other of an upper edge 21, 25 or a lower edge 23, 27. In this way, if a ball hits a lower edge 23, 27 at a location above the center of the ball, the ball will likely deflect downwardly and away from the wearer. If a ball strikes a lower edge 23, 27 below the center of the ball, the ball will likely deflect upwardly and roll over an upper edge 21, 25 and thence deflect away from the wearer. A ball striking an upper edge 21, 25 without striking a lower edge will do so below its center and thereby deflect upwardly over the guard portion and away from the wearer.

Figure 7:
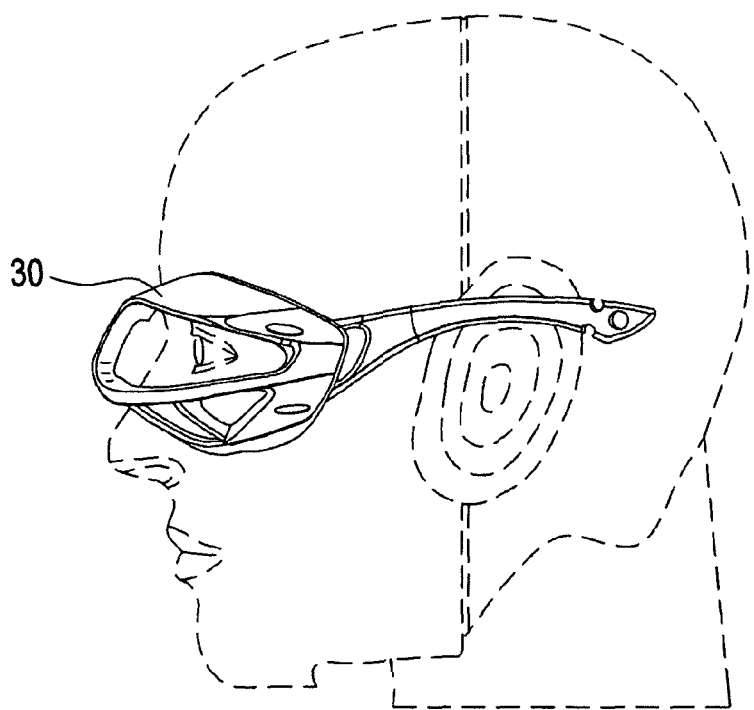
FIG. 7 shows a side view of the face and eye guard device as worn.
Figure 8:
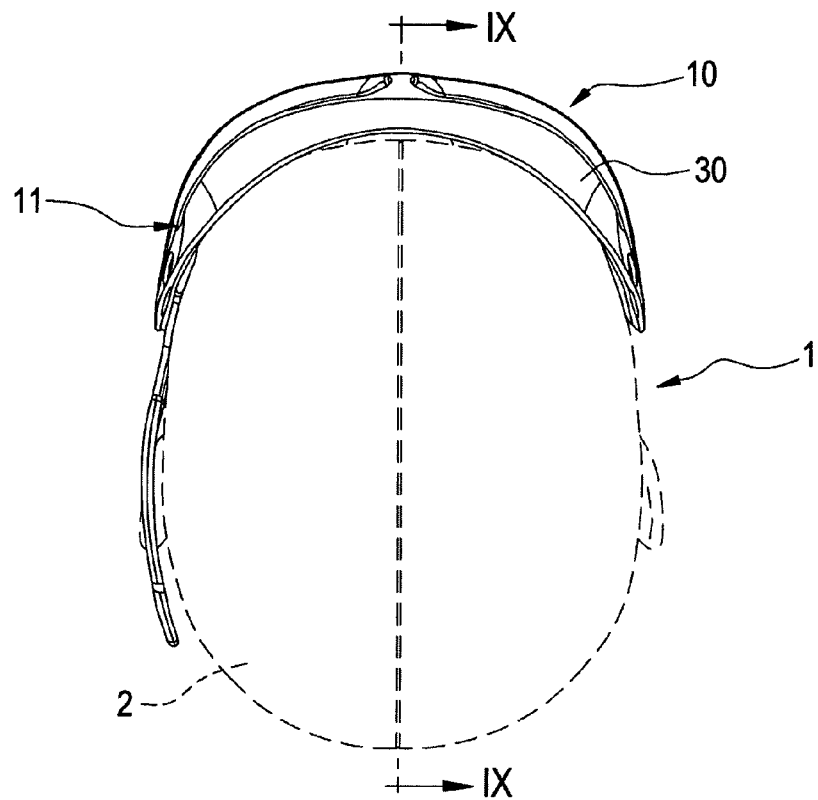
FIG. 8 shows a top view of the face and eye guard device as worn.
Figure 9:
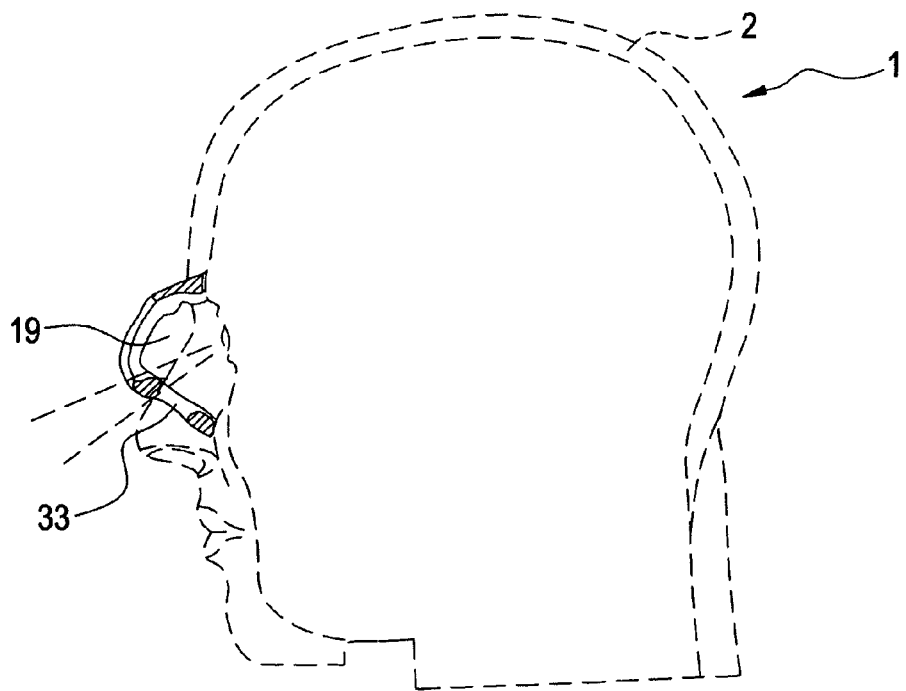
FIG. 9 shows a cross-sectional view along the line IX-IX of FIG. 8.

As best seen in FIGS. 1 and 3, above the upper edges or bars 21 and 25 of the openings 17 and 19, the guard device 11 includes a visor portion 30 extending in an arcuate path completely laterally across the device 11. The visor can be considered an integral extension of the bars 21 and 25. As understood from FIG. 3 as well as FIG. 8, the visor portion 30 creates spacing between the openings 17 and 19 and the head 2 of the user 1. This spacing facilitates deflection of the ball over the head 1 of the user in the scenarios described above. FIG. 7, in particular, shows the angled configuration of the visor portion 30 that assists in deflecting a lacrosse ball away from the head of the user.

Figure 6:
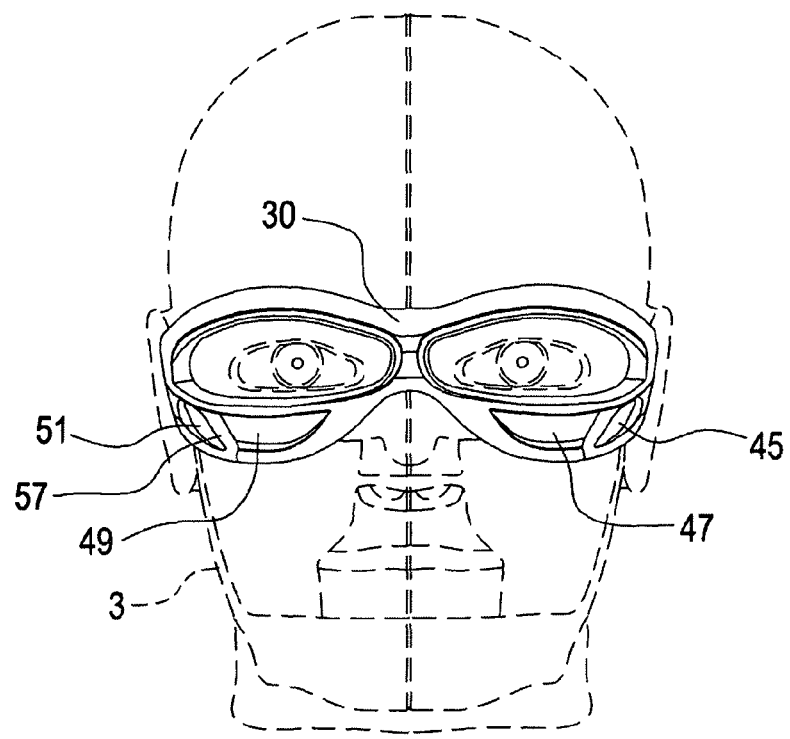
FIG. 6 shows a front view of the inventive face and eye guard device as worn.

As best seen in FIGS. 2 and 6, the guard device 11 includes an arcuate bottom edge 33 that may be sized to smoothly engage the nose 3 of the user. The edge 33 curves around at locations 35 and 37 as shown in FIG. 2 in an aesthetically pleasing manner. Adjacent the locations 35 and 37, soft padding 39 and 41 is adhered onto surfaces 38 and 40 extending upwardly from said bottom edge, respectively, to cushion engagement of the device 11 on the face of the user. Similar soft padding 43 is provided on the surface 42 of the device that is immediately downward of the visor portion 30. This padding 39, 41 and 43 is made of any suitable material including a soft foam, a closed cell foam, or a foam having an outer skin and an inner foam center.

With further reference to FIGS. 2 and 6, the edge 33 and surfaces 38 and 40 underlie openings 45, 47, 49 and 51. As seen in FIG. 2, the opening 45 is designed in part by the portion 40 and the edge 23 as is the case of the opening 47. The openings 45 and 47 are separated by a vertical bar 53. Above the vertical bar 53 is a further vertical bar 55 that separates the eye opening 17 from a side opening 18. Similarly, the openings 49 and 51 are defined between the portion 38 and the lower edge 27 of the opening 19. A vertical bar 57 (FIG. 6) separates the openings 49 and 51 from one another, and an additional vertical bar 59 separates the eye opening 49 from a further side opening 20. The openings 18 and 20 and the vertical bars 55 and 59 are also seen with reference to FIG. 1. The eye openings 17 and 19 are separated by a central vertical bar 60.

The structure described above including a plurality of openings defined by vertical bars and horizontal portions is specifically designed to combine structural integrity and lightweight construction while also being aesthetically pleasing. These vertical bars may also be described as "struts."

FIG. 4 shows the left temple 13 which includes a curved body 63, attachment members 65 and 67 provided in a branched configuration, and a rear portion 69 with an opening 64 therethrough. Grooves 66 and 68 are just forward of the opening 64 for a purpose to be described in greater detail hereinafter.

FIG. 5 shows the temple 15 which is seen to include an arcuate body 73, attachment members 75 and 77, and a rear portion 79 where holes 74 and 76 are provided for a purpose to be described in greater detail hereinafter.

With reference back to FIG. 1, the device 11 includes openings 80 and 82 on the left side thereof which releasably receive the attachment members 65 and 67, respectively, of the left temple 13. As should be understood, similar openings are provided on the right side of the device 11 to similarly receive the attachment members 75 and 77 of the temple 15.

With reference to FIG. 3, the purposes for the holes 64, 74 and 76 and the grooves 66 and 68 will now be explained. As shown in FIG. 3, an elastic strap 81 is provided which comprises a continuous loop of elastic material. As understood from FIG. 3, the strap 80 is installed on the temples 13 and 15 in the following manner: A portion 83 of the loop 81 is engaged within the grooves 66 and 68, and the rest of the loop 81 is inserted through the opening 64. The loop is then inserted through the opening 76 and looped around at 85 and inserted through the opening 74. The portion 87 of the loop 81 is located as shown in FIG. 3. By pulling more of the loop 81 through the holes 76 and 74, or less as the case may be, the amount of material 89 of the loop 81 may be increased or decreased, as the case may be, to thereby adjust the strength by which the loop 81 holds the device 10 on the head of the user. The loop 81 may be made of any suitable flexible elastic material.

The temples 13 and 15 are preferably molded out of a rubbery material such as Dupont HYTRAL™. The device 11 is preferably molded of a hard plastic material, such as, for example, impact modified polycarbonate or polycarbonate/PBT alloy. Of course, other suitable materials may be used for the inventive device 11 including any desirable hard plastic material exhibiting the combination of high strength, light weight, and easy moldability as well as reasonable pricing. Lightweight metals such as magnesium, aluminum and titanium may also be employed.

As explained above, the dimension X shown in FIG. 3 defines the forward to rearward displacement between the upper edges 21, 25 of the openings 17 and 19, respectively, and the lower edges 23 and 27 thereof. The preferred value for the dimension X is 0.55 inches to 0.85 inches, although Applicants have found that keeping those dimensions between 0.25 inches and 1.25 inches will result in effective performance.

FIG. 2 displays the dimensions Y and Z within the opening 17 which are also intended to equally apply to the opening 19. In the preferred embodiment of the present invention, the dimension Y should be within the range of 2.0 to 2.75 inches, while the dimension Z should be within the range of 0.75 to 1.25 inches. The ideal dimensions for Y and Z are 2.5 inches and 1 inch, respectively. The width dimension Y is designed to permit each eye of the user to have clear vision up to 45 degrees to either side of the center of the eye as viewed through the respective openings 17, 19. The lower edges or bars 23, 27 of the openings 17 and 19 comprise generally horizontally disposed ribs that are in the range of 0.25 to 0.45 inches in thickness.

The dimensions of the visor portion 30, openings 17 and 19, and bars 23 and 27 are specifically devised as best can be accomplished so that when the inventive head and eye guard device 10 is worn by the user, the distance between the outer edge of the eyeball and the lower bar 23 or 27 of the device 11 is sufficient to preclude touching of the eyeball by either edge or the ball. In one experiment using a Canadian Standards Association (CSA) juvenile headform as specified in ASTM-F803-03, this dimension was found to be within the range of 1.25 to 1.75 inches, preferably about 1.45 inches.

The present invention is highly advantageous over the prior art. It avoids the use of plastic lenses which can scratch and obscure vision. It avoids the vision obscuring nature of wire face masks. It is extremely lightweight and extremely strong. The inventive device is aesthetically pleasing and is engineered to preclude a lacrosse ball from passing through the eye openings thereof and engaging the user's eye. In designing the present invention, Applicants performed significant studies, some of which employed the use of high speed film. Those studies showed that when a lacrosse ball made of solid rubber, having a diameter of 2.5 inches and weighing 8 ounces makes contact with a face guard, it deforms considerably at the 60 mile per hour test speed. During this deformation, the ball becomes oblong. Thus, it is important to ensure that the distance dimension Z is sufficiently narrow enough that an oblong lacrosse ball as deformed on impact cannot achieve dimensions small enough to squirt through the upper and lower edges of the eye openings and engage the eye. Applicants have found that maintaining the dimension Z within the range described above, namely, a dimension less than 1.25 inches, is sufficient for this purpose.

Moreover, as explained above, the dimension X seen in FIG. 3 was designed, through extensive experimentation, to be maintained between 0.25 inches and 1 inch and preferably within the range of 0.55 to 0.85 inches to further deter any possibility that a lacrosse ball will pass through any eye opening. Rather, when the ball engages one of the lower openings, the tendency is for the ball to be deflected away from the head of the user as explained above.

In considering the design of the dimension Z, it is remarkable to note that the diameter of a lacrosse ball is approximately 2.5 inches, yet the dimension Z must be maintained to, at most, half that diameter to preclude the ball from passing through one of the openings 17 or 19. This demonstrates the degree to which the ball may change shape upon impact.

The alignment of the struts 53 and 55 as well as the struts 51 and 59 assists in strengthening the device 11, but other configurations are equally possible.

As explained above, while the inventive face and eye guard device 10 is disclosed in terms of a preferred embodiment usable through its specific dimensions and configuration for the sport of women's lacrosse, the invention can also be adapted to other sports. The present invention is also applicable in other sports such as field hockey, basketball, softball, tennis, racketball, badminton, and others.

As such, an invention has been disclosed in terms of a preferred embodiment thereof which fulfills each and every one of the objects of the invention as set forth hereinabove, and provides a new and useful face and eye guard device of great novelty and utility.

Of course, various changes, modifications and alterations in the teachings of the present invention may be contemplated by those skilled in the art without departing from the intended spirit and scope thereof.

As such, it is intended that the present invention only be limited by the terms of the appended claims.

The invention claimed is:

1. A face and eye guard device, comprising:
   a) a guard portion including two openings for eyes of a wearer;
   b) each of said openings being defined by two vertically spaced horizontal bars comprising an upper bar and a lower bar and defining an opening therebetween through which a user may see, said openings being separated by a vertical strut;
   c) said upper bar being displaced rearwardly with respect to said lower bar with respect to a head of a wearer such that when a projectile strikes said device, said projectile strikes said upper or lower bar and is deflected away from said device in a controlled path and does not project through said at least one opening.

2. The device of claim 1, further including a visor portion extending rearward from each said upper bar.

3. The device of claim 2, wherein said visor portion extends laterally across said device and rearwardly and upwardly to a terminating rear edge adjacent a wearer's face.

4. The device of claim 3, further including a first face engaging surface depending downwardly from said rear edge of said visor portion.

5. The device of claim 4, wherein said face engaging surface comprises a resilient material.

6. The device of claim 4, further including a bottom edge extending across said device and including an arcuate section that may be configured to rest on a wearer's nose.

7. The device of claim 6, further including a second face engaging surface extending upwardly from said bottom edge.

8. The device of claim 7, wherein said face engaging surfaces comprise a resilient material.

9. The device of claim 1, further including a bottom edge extending across said device and including an arcuate section configured to rest on a wearer's nose.

10. The device of claim 9, further including a face engaging surface extending upwardly from said bottom edge.

11. The device of claim 10, wherein said face engaging surface comprises a resilient material.

12. The device of claim 1, further including a temple on each side of said guard portion, each temple configured to sit on top of an ear of a wearer.

13. The device of claim 12, wherein each temple has a rear termination extending behind an ear of a wearer, and a flexible strap connected between said rear terminations.

14. The device of claim 12, wherein said temples are made of soft plastic.

15. The device of claim 1, wherein said guard portion is made of hard plastic.

16. The device of claim 1, wherein said lower bar is spaced from an eyeball of a wearer a distance sufficient to preclude said lower bar or a projectile from striking said eyeball.

17. A face and eye guard device, comprising:
   a) a guard portion including two openings for eyes of a wearer separated by a vertical strut;
   b) each of said openings being defined by two vertically spaced horizontal bars comprising an upper bar and a lower bar and defining an opening therebetween through which a user may see;
   c) each said upper bar being displaced rearwardly with respect to a respective said lower bar with respect to a head of a wearer such that when a projectile strikes said device, said projectile strikes said upper or lower bar and is deflected away from said device in a controlled path and does not project through one of said openings;
   d) a visor portion extending rearward from each said upper bar; and
   e) a temple on each side of said guard portion, each temple configured to sit on top of an ear of a wearer.

18. The device of claim 17, wherein said visor portion extends laterally across said device and rearwardly and upwardly to a terminating rear edge adjacent a wearer's face.

19. The device of claim 18, further including a face engaging surface depending downwardly from said rear edge of said visor portion, said face engaging surface comprising a resilient material.

20. The device of claim 17, wherein each temple has a rear termination extending behind an ear of a wearer, and a flexible strap connected between said rear terminations.

* * * * *